United States Patent
Modabber et al.

(10) Patent No.: US 11,457,979 B2
(45) Date of Patent: Oct. 4, 2022

(54) SURGICAL PLANNING SYSTEM FOR THE RECONSTRUCTION OF MISSING OR DAMAGED BONE PARTS

(71) Applicant: RHEINISCH-WESTFÄLISCHE TECHNISCHE HOCHSCHULE (RWTH) AACHEN, Aachen (DE)

(72) Inventors: Ali Modabber, Aachen (DE); Stefan Raith, Passau (DE)

(73) Assignee: RHEINISCH-WESTFÄLISCHE TECHNISCHE HOCHSCHULE (RWTH) AACHEN, Aachen (DE)

( * ) Notice: Subject to any disclaimer, the term of this patent is extended or adjusted under 35 U.S.C. 154(b) by 104 days.

(21) Appl. No.: 16/771,582

(22) PCT Filed: Dec. 11, 2018

(86) PCT No.: PCT/EP2018/084264
§ 371 (c)(1),
(2) Date: Jun. 10, 2020

(87) PCT Pub. No.: WO2019/115486
PCT Pub. Date: Jun. 20, 2019

(65) Prior Publication Data
US 2020/0297421 A1 Sep. 24, 2020

(30) Foreign Application Priority Data

Dec. 11, 2017 (DE) .......................... 102017222368.5

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 34/30* (2016.02); *G06T 7/0012* (2013.01);
(Continued)

(58) Field of Classification Search
CPC ......... A61B 34/10; A61B 34/20; A61B 34/30; A61B 2034/105; A61B 2034/107;
(Continued)

(56) References Cited

U.S. PATENT DOCUMENTS

| 2004/0068187 A1* | 4/2004 | Krause | ................. | A61B 17/151 |
| | | | | 600/443 |
| 2004/0102866 A1* | 5/2004 | Harris | ..................... | G06T 17/00 |
| | | | | 700/98 |

(Continued)

FOREIGN PATENT DOCUMENTS

| WO | WO 2013/087082 | 6/2013 |
| WO | WO 2014/188369 | 11/2014 |

(Continued)

OTHER PUBLICATIONS

Translated International Preliminary Report on Patentability for International (PCT) Patent Application No. PCT/EP2018/084264, dated Jun. 16, 2020, 8 pages.

(Continued)

*Primary Examiner* — Emily C Terrell
*Assistant Examiner* — Molly Wilburn
(74) *Attorney, Agent, or Firm* — Sheridan Ross P.C.

(57) ABSTRACT

A surgical planning system for the reconstruction of missing or damaged bone parts comprises processing circuitry for receiving 3D image data regarding at least one osseous donor area, processing the 3D image data into structured 3D image data where osseous portions are distinguished from soft tissues and/or vascular systems, reading in of 3D target (Continued)

data regarding a missing or damaged bone part, obtaining one or more 3D target curves in relation to the 3D target data and the 3D image data of the at least one osseous donor area, and segmenting the structured 3D image data with the osseous portions of the osseous donor area into segments, where the segments within the structured 3D image data are determined based on the 3D target data and an adaptation of sections of the one or more 3D target curves.

15 Claims, 5 Drawing Sheets

(51) Int. Cl.
*A61B 34/30* (2016.01)
*G06T 7/187* (2017.01)
*G06T 7/11* (2017.01)
*G06T 7/00* (2017.01)

(52) U.S. Cl.
CPC ............... *G06T 7/11* (2017.01); *G06T 7/187* (2017.01); *A61B 2034/105* (2016.02); *A61B 2034/107* (2016.02); *G06T 2207/10081* (2013.01); *G06T 2207/10104* (2013.01); *G06T 2207/10108* (2013.01); *G06T 2207/10136* (2013.01); *G06T 2207/30008* (2013.01)

(58) Field of Classification Search
CPC ........ A61B 2017/00969; G06T 7/0012; G06T 7/11; G06T 7/187; G06T 2207/10081; G06T 2207/10104; G06T 2207/10108; G06T 2207/10136; G06T 2207/30008
See application file for complete search history.

(56) References Cited

U.S. PATENT DOCUMENTS

| | | | | |
|---|---|---|---|---|
| 2010/0274534 A1* | 10/2010 | Steines | ............... | A61F 2/30942 703/11 |
| 2011/0305379 A1* | 12/2011 | Mahfouz | ............... | A61F 2/3859 345/419 |
| 2013/0296872 A1* | 11/2013 | Davison | ............. | A61B 17/1728 606/87 |
| 2014/0195205 A1* | 7/2014 | Benker | ................... | G06F 30/00 703/1 |
| 2014/0244220 A1* | 8/2014 | McKinnon | .............. | G06F 30/00 703/1 |
| 2015/0051876 A1* | 2/2015 | Rueber | .................. | A61B 17/80 703/1 |
| 2015/0223900 A1* | 8/2015 | Wiebe, III | .............. | G06F 30/00 703/11 |

FOREIGN PATENT DOCUMENTS

| WO | WO 2015/081232 | 6/2015 |
|---|---|---|
| WO | WO 2017/162444 | 9/2017 |

OTHER PUBLICATIONS

Translated Written Opinion for International (PCT) Patent Application No. PCT/EP2018/084264, dated Mar. 8, 2019, 7 pages.
Translated International Search Report for International (PCT) Patent Application No. PCT/EP2018/084264, dated Mar. 8, 2019, 3 pages.

\* cited by examiner

SURGICAL PLANNING SYSTEM FOR THE RECONSTRUCTION OF MISSING OR DAMAGED BONE PARTS

CROSS REFERENCE TO RELATED APPLICATIONS

This application is a national stage application under 35 U.S.C. 371 and claims the benefit of PCT Application No. PCT/EP2018/084264 having an international filing date of 11 Dec. 2018, which designated the United States, which PCT application claimed the benefit of German Patent Application No. 10 2017 222 368.5 filed 11 Dec. 2017, the disclosures of each of which are incorporated herein by reference in their entirety.

The invention relates to a surgical planning system for the reconstruction of missing or damaged bone parts.

PRIOR ART

The reconstruction of bones or bones and tissue parts—whether to restore a cosmetic appearance or to restore a function—is a constantly recurring case in medicine.

The reasons necessitating a restoration might be, e.g., that tissue and bone parts had to be removed on account of benign or malignant growths or have been lost or damaged as a result of an accident, or that they show congenital deformities.

In these cases, OP planning systems have already been used in the past.

For example, refer to the international patent application WO 2014/188 369 A1, which shows a method for the planning of a surgical procedure in which a three-dimensional image of at least a part of a donor bone is initially prepared. The bone thus defines an outer three-dimensional surface. One or more sensitive anatomical structures are identified which must not be involved in the bone harvesting. In this way, the volume of the bone suitable for the donation is identified, with exclusion of sensitive anatomical structures and bounding of the volume by a portion of the outer surface of the bone. The parameters for the surgical procedure are basically acquired by identifying a guide surface.

However, this method is quite computationally intensive and does not permit fast OP planning. This is due, among other things, to the fact that volume computations are performed. Furthermore, this method does not allow the definition of curves running along anatomically relevant structures.

Moreover, the system is not suitable for considering the complexity of the target space in a suitable manner.

While it has been known since the late 1980s how to employ computer-assisted surgery, the methods known thus far, which are based on pre-bent plates or tissue structures or transplant cutting templates, are time-consuming and relatively imprecise. Even so, these methods are advantageous compared to traditional surgical methods, since they generally reduce ischemic time and/or the size of the donor area and often provide a better functional and/or aesthetic outcome. However, this outcome still remains heavily dependent on the surgeon and his experience.

Meanwhile, software approaches have been developed to support a step by step guidance, but the expense is still enormous, and the surgical planning is only assisted by the guidance. Therefore, the surgical planning generally requires an appropriately clinically trained engineer, who is generally involved by means of joint planning (such as a conference call). The clinically trained engineer will prepare in advance the segments for use by the surgeon. In such a setting, the surgeon can then "access" these predetermined segments during the surgical planning. In the course of the discussion, the surgeon will discuss a certain number of bone incisions and their position, with the number and position of the incisions and their subsequent arrangement being left to the sole discretion and experience of the surgeon. The method is therefore highly user-dependent, and an objectification of this method is not possible.

Although a better outcome can be virtually achieved with a plurality of segments, the likelihood of bone necrosis due to inadequate metabolism also increases with the number of bone incisions.

Starting from this, one problem which the invention proposes to solve is to provide a surgical planning system which avoids one or more shortcomings of the prior art and provides an improved and/or a simpler system.

BRIEF PRESENTATION OF THE INVENTION

The problem is solved by a surgical planning system for the reconstruction of missing or damaged bone parts, comprising a device for reading in of 3D image data regarding at least one osseous donor area, means for processing the 3D image data into structured data so that osseous portions are distinguished from soft tissues and/or vascular systems, means for reading in of 3D target data regarding a missing or damaged bone part, means for obtaining one or more 3D target curves in relation to the 3D target data and/or the 3D data of the donor area, means for segmentation of the osseous portions of the osseous donor area, and means for merging the segments into a reconstruction, wherein the segmentation of the osseous portions adapts 3D target curves to 3D surfaces of the 3D target data.

Further advantageous configurations are the subject matter of the dependent claims and the detailed specification, as well as the figures.

BRIEF PRESENTATION OF THE FIGURES

The invention shall be explained more closely in the following, making reference to the exemplary embodiments shown in the figures.

DETAILED SPECIFICATION

Figure 1:
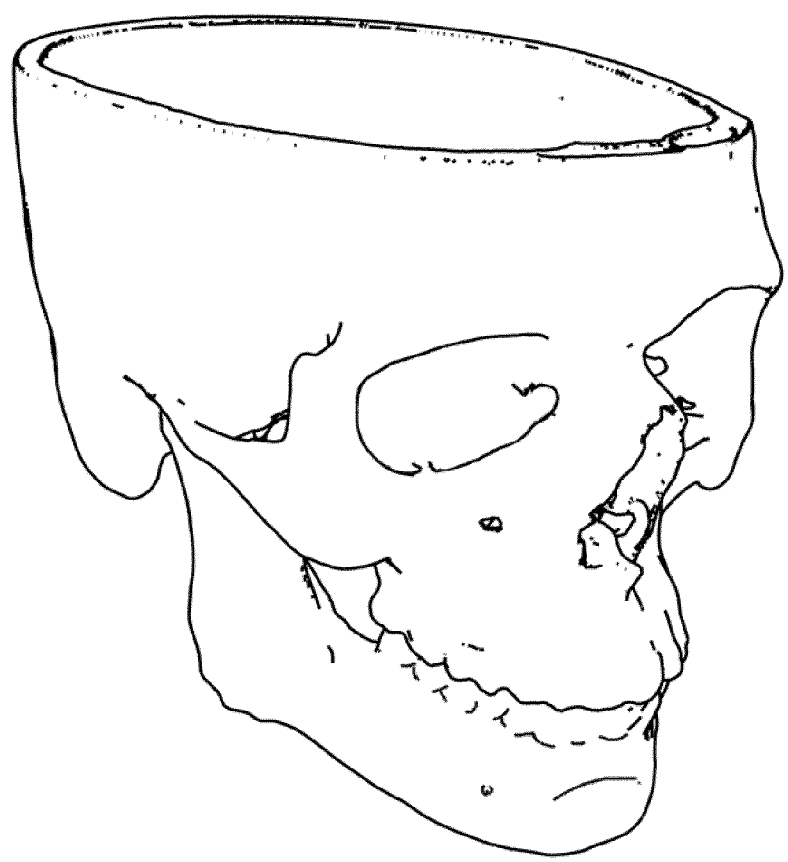
FIG. 1 shows a schematic representation of a target region.

The invention shall be represented more closely in the following, making reference to the figures. It should be noted that different aspects are described which may each be used alone or in combination, i.e., any aspect can be used with different embodiments of the invention, as long as it is not presented as a pure alternative.

Furthermore, for sake of simplicity in the following we generally only mention one entity. Unless explicitly noted, however, the invention may also comprise several of the mentioned entities. Accordingly, the use of the words "a" and "an" should be understood as merely indicating that at least one entity is used in a single embodiment.

According to embodiments of the invention, a surgical planning system is provided for the reconstruction of missing or damaged bone parts.

The surgical planning system comprises at least one device for reading in of 3D image data regarding at least one osseous donor area. For example, voxel data can be obtained directly from a corresponding imaging device and/or voxel data can be read in from previously obtained (processed) image data. For this, e.g., suitable interfaces or readers for storage media can be provided.

The surgical planning system furthermore comprises means for processing the 3D image data into structured data, so that osseous portions are distinguished from soft tissues and/or vascular systems. For this, an intensity and/or an intensity change and/or an edge filter, etc., can be used. This will make it possible to selectively represent, selectively select, etc., certain structures identified from the structured image data, such as bones and/or vessels and/or muscle portions and/or fatty tissue. Such means can be provided by a suitably programmed processing unit and/or in hardware and/or a mixture of hardware and software.

The surgical planning system furthermore comprises means for reading in of 3D target data regarding a missing or damaged bone part. For example, voxel data can be obtained directly from an appropriate imaging device and/or voxel data can be read in from (processed) previously obtained image data. For this, e.g., suitable interfaces or readers for storage media can be provided. Thus, e.g., it is possible to obtain data by mirroring of a "healthy" area, by selection from a database, by manual modeling and/or a mixture of these. It should be noted that individual differences can be explored by suitable post processing (stretching/compressing/rotating), e.g., in order to capture or compensate for other malformations and/or take clinical or surgical restrictions into account.

The surgical planning system furthermore comprises means for obtaining one or more 3D target curves in relation to the 3D target data and/or the 3D data of the donor area. These reading means may be prepared, e.g., from the previously obtained 3D target data and/or interactively by a surgeon, e.g., based on the previously obtained 3D target data. It is especially worth noting here that the target curves are curves in 3D space. Thanks to the use of curves, the data processing in later steps can be significantly easier and faster.

The surgical planning system furthermore comprises means for segmentation of the osseous portions of the osseous donor area. On the basis of the 3D target data and an adaptation of segments of the target curve to the 3D target data, segments can be determined in the structured 3D image data that show a certain (desired/predetermined) match. Different parameters can be taken into account, such as the minimum size of a segment, the maximum number of segments, or the maximum deviation from the target curve, to mention only a few. Based on these boundary conditions, different segmentations can be proposed which can then if necessary be processed for further evaluation by the surgeon. As one exemplary implementation, variations can be generated by fuzzy operations, such as multiplication or addition of random variables.

The surgical planning system furthermore comprises means for merging the segments into a reconstruction, wherein the segmentation of the osseous portions adapts 3D target curves to 3D surfaces of the 3D target data. By means of the (virtual) reconstruction thus created, the surgeon can select one possible variant and/or iteratively refine it based on his experience and knowledge of the patient.

That is, in contrast with known methods, in the method according to the invention the recipient region is now explicitly taken into consideration. Unlike known systems in which computationally intensive planning is performed with reference to surface data and/or volume data, in the system according to the present invention a space curve is determined which can orient itself to anatomical curves.

FIG. 1 shows, e.g., part of a skull with a lower jaw. Now, e.g., if part of the patient's lower jaw is damaged, this part could be reconstructed from other osseous elements.

Figure 2:
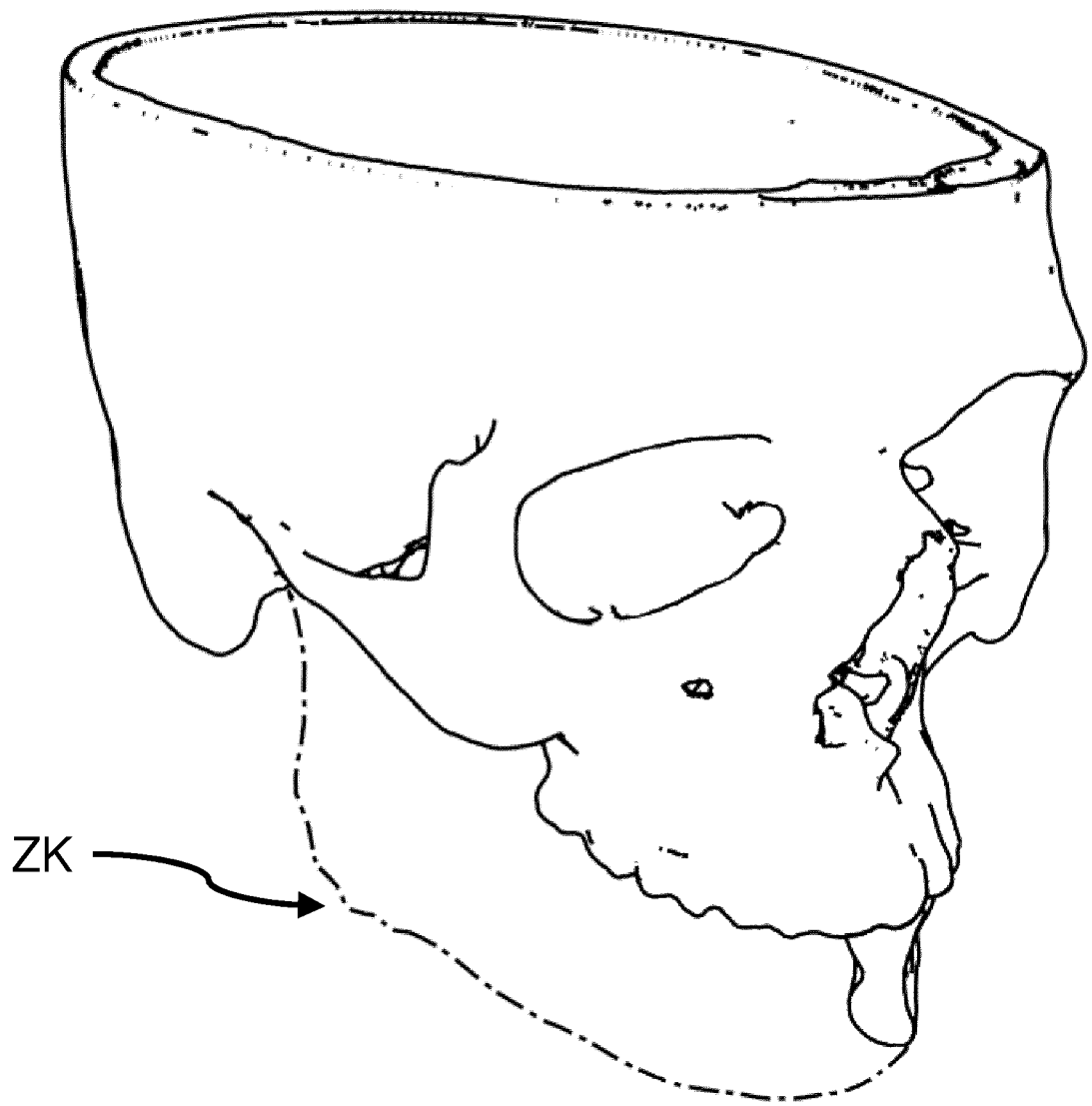
FIG. 2 shows a schematic representation of a target curve.

For example, the broken line in FIG. 2 shows one possible target curve ZK, which may be obtained, e.g., with the aid of previous image data and/or from a library and/or from a mirroring of the left lower jaw onto the right side.

Even though it may appear at first glance that the target curve ZK basically reproduces the outermost line of the target area, this need not always be the case. For example, other anatomical boundaries may be the basis for the choice, e.g., for implants, etc., at individual points or sections. However, it is also possible to define more than one target curve. Using the example of a lower jaw, it would be possible, e.g., to define a first target curve, indicating the (aesthetically) determining margin, while a second target curve indicates, e.g., a desired profile, which would be advantageous for tooth implants, for example. Other parameters, such as the providing for vascular systems/soft tissues, may be considered in addition.

Figure 3:
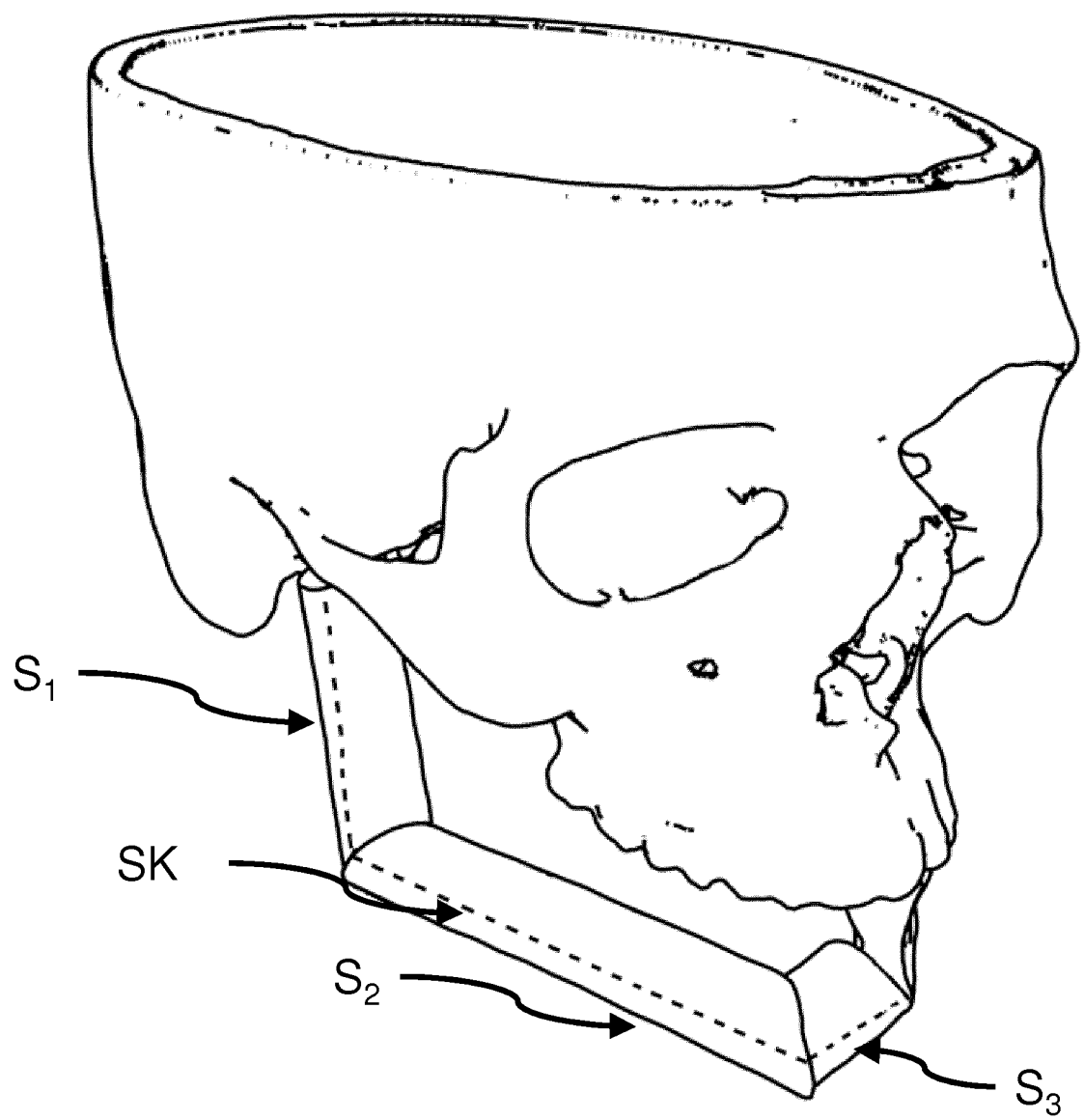
FIG. 3 shows a schematic representation of segments with a generated curve according to one embodiment of the invention.
Figure 4:
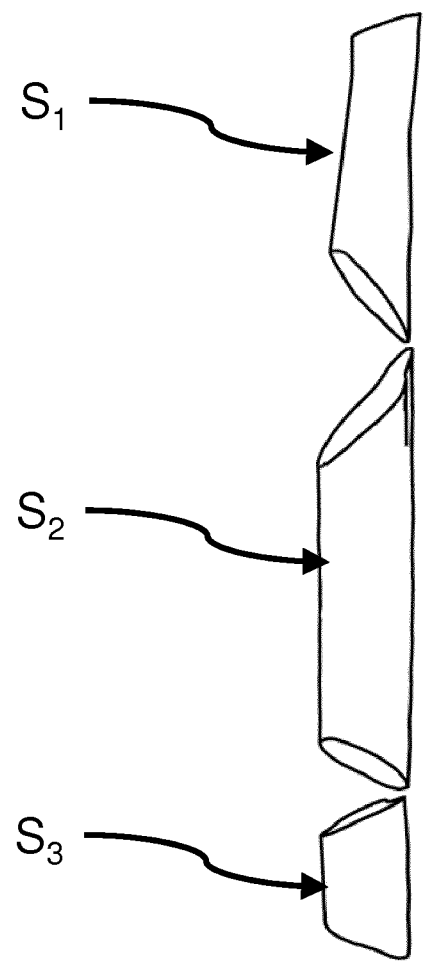
FIG. 4 shows a schematic representation of segments of a donor area which are used in the representation of FIG. 3.
Figure 5:
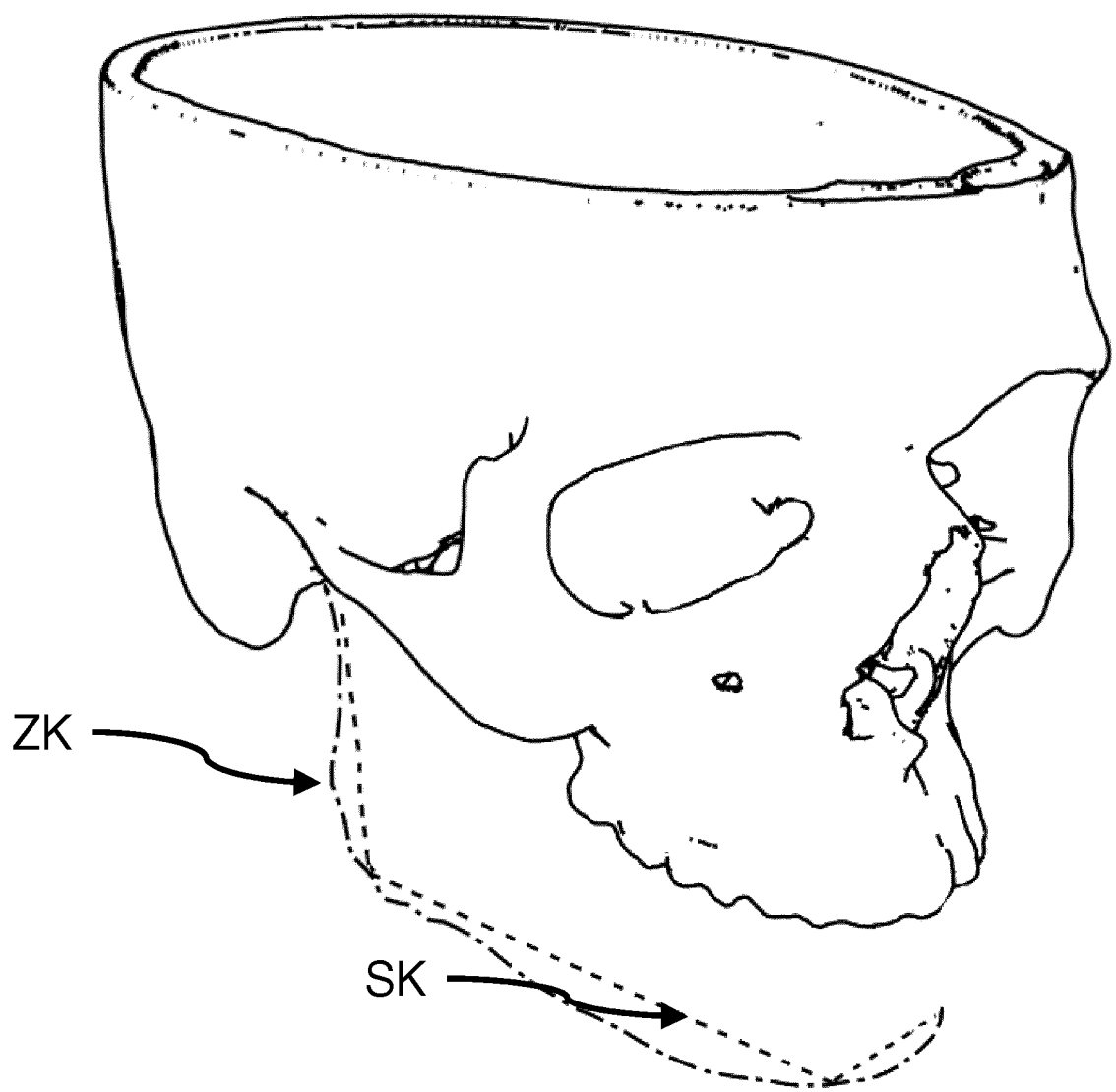
FIG. 5 shows a schematic comparison of target curve and achievable curve.

FIG. 3 thus shows an example of how segments from a donor area, for example, are adapted to the target curve. For example, this shows a reconstruction with the aid of three segments $S_1$, $S_2$, $S_3$. These three segments S1, S2, S3 are taken from a donor area, here, a fibula per FIG. 4. The corresponding curve SK is shown here by a broken line. The comparison between the target curve SK so obtained (broken line) and the original target curve ZK is shown in FIG. 5.

In other words, the invention relates to a system and a method for the planning of bone reconstructions with autologous or allologous transplants in which 3D data obtained from the donor and recipient is used by means of triangulation to produce surface representations of the donor and the recipient region, with at least one (contour) line defined on the donor and recipient surface in each case, wherein the (contour) line can be adapted with the aid of the curvature of the respective surface to the transplant and the reconstruction.

The system and method developed make possible a computer-assisted planning of bone reconstructions, especially in the field of facial surgery.

The explicit innovation of the method is the use of three-dimensional curves which are oriented to the individual bone geometries of the patient. These curves are generally produced either manually or automatically (computer-assisted) both on the transplant bone and on the planned recipient region, thereby affording the possibility of a simplification of the complex three-dimensional surface geometry of the bone. This simplification makes possible an at least partly automated planning of the reconstruction. On this basis, cutting templates and individualized plating systems can be created as needed, which simplify and speed up the operating procedure and thus can lead to a better surgical outcome.

In one embodiment of the invention, the planning comprises adjustable minimum sizes for the segments. For example, it can thus be avoided that segments are proposed which are so small upon separation that the vascular supply is not assured and there is a danger of necrosis.

In a further embodiment of the invention, the planning comprises an adjustable maximum size for the segments. It the size of a segment is chosen to be too large, there is generally a risk of the deviation from the target curve becoming too large.

In a further embodiment of the invention, the system may furthermore comprise means of creating structural data for a surgical template for use in a later surgery. For example, such a template can establish a donor area and indicate cutting edges, so that the segments can be created according to the (selected) segmentation. For example, appropriate cutting planes can be specified by the template, so that the segments can be created from a fibula, for example (as shown in FIG. 4).

The structural data for a surgical template may be structural data for a 3D printer. In this case, it is possible to create such a template by a specialized manufacturer as well as locally on site.

A special advantage of the system is that it allows the segmentation and planning to also allow for soft tissues and/or vascular systems, thanks to the structuring of the 3D image data. For example, it is thus possible to take into account a possible soft tissue portion already at the time of the planning, which is aesthetically advantageous to the reconstruction. Likewise, alternatively or additionally, vessels may be taken into account that will be needed for the subsequent supply of bones and other tissue. If these are already taken into account from the donor area, the surgery time can be shortened. Shorter surgery time generally has a positive impact on the healing process.

The surgical planning system according to the invention can create a number of proposals for a segmentation by means of easily variable boundary conditions wherein one, several, or all of the proposals are visualized for a selection. That is, the surgeon can select the one proposal which appears most advisable for the patient. Thus, e.g., it may happen that a functionally and/or aesthetically better reconstruction is made possible with one more segment and only a slightly longer surgery time. The surgeon may then select this somewhat more extensive proposal if he deems it appropriate. Furthermore, a computer-assisted quantification of the match between planning and target geometry can be provided, which will be part of the decision-making process.

According to a further embodiment of the invention, the surgical planning system furthermore provides means for the simultaneous visualization of the 3D target data and the reconstruction produced by segmentation. One example of such a visualization is shown in FIG. 5. Visualizations can be provided, e.g., on a monitor or a virtual reality system.

According to a further embodiment of the invention, the 3D image data can be data from computer tomography and/or MRT, MRT-angio and/or PET/CT, SPECT/CT, CT-angio, digital volume tomography, and 3D sonography, although not being limited to these. Obviously, "fused" image data from different methods and/or structural data from other software tools can be used.

According to yet another embodiment of the invention, the 3D target data comprises copying and/or mirroring and/or relative repositioning of corresponding missing or damaged bone parts of the same patient or is generated from an anthropometric geometry database. A relative repositioning may be of advantage, e.g., in the case of compound fractures.

Without limiting the generality of the invention, it is also possible to provide data for a robot-assisted surgery and/or real-time navigated surgery from the surgical planning system. That is, data from the surgical planning system can be used in the surgery, especially in the segmentation of the donor area, but also in the repositioning in the target area, for example to make possible the most precise possible course of the surgery. In this case, data can be fed into imaging systems and/or positioning tasks can be assisted.

It is of special benefit that the proposed surgical planning system according to the invention has diverse applications. Thus, the system allows the missing or damaged bone parts to be parts of either a mandibula, a maxilla, a zygoma, a cranium, a hand bone, a foot bone, a tibia, a humerus, a femur, a radius or an ulna.

It is of special benefit that the proposed surgical planning system according to the invention has diversified applications. Thus, the system allows the osseous donor area to be an iliac crest and/or a scapula and/or a fibula and/or a radius and/or a femur and/or a rib and/or a cranium and/or a tabula externa.

The system can easily also take different donor areas into account for a target area, however. Thus, e.g., it can investigate whether an alternative donor area or a mixture of segments from different donor areas might provide a better outcome under the circumstances.

With the proposed method, it is now possible to make use of relatively inexpensive hardware, since the demands on the computing power are lower due to fewer demands. Since, furthermore, both the donor area and the target area are taken into account, the outcome is comparable to or better than previous systems. At the same time, thanks to the structuring, the overall outcome can be significantly improved due to the additionally possible consideration of other tissues/vessels.

An extensive automation is made possible by the surgical planning system, so that empirical values can be used as boundary values, thus making possible an improved selection, even by a less experienced surgeon.

In particular, the system can indicate which parts of a donor area to use and how they are to be used, with the number, location, and direction of bone cuts, and thus also the number of usable segments, able to be determined. The complexity can be kept so low that a timely surgical planning can be carried out so with conventional computer hardware. This is made possible by the fact that the geometrically poorly conditioned problem of arrangement of surfaces with different curvatures is reduced to an arrangement of spatial curves. This also enables user interactions with respect to parameters/boundary values.

What is claimed is:

1. A surgical planning system for the reconstruction of missing or damaged bone parts, comprising:
    processing circuitry for:
        receiving 3D image data regarding at least one osseous donor area;
        processing the 3D image data into structured 3D image data where osseous portions are distinguished from soft tissues and/or vascular systems;
        reading in of 3D target data regarding a missing or damaged bone part;
        obtaining one or more 3D target curves in relation to the 3D target data and the 3D image data of the at least one osseous donor area;
        segmenting the structured 3D image data with the osseous portions of the at least one osseous donor area into segments, wherein the segments within the structured 3D image data are determined based on the 3D target data and an adaptation of sections of the one or more 3D target curves; and merging the segments into a reconstruction, wherein the segmentation adapts the one or more 3D target curves to 3D surfaces of the 3D target data.

2. The surgical planning system according to claim 1, wherein the segmentation comprises adjusting sizes for the segments.

3. The surgical planning system according to claim 1, wherein the segmentation comprises adjusting maximum sizes for the segments.

4. The surgical planning system according to claim 1, wherein the processing circuitry creates structural data for a surgical template for use in a subsequent surgery.

5. The surgical planning system according to claim 4, wherein the structural data for a surgical template is structural data for a 3D printer.

6. The surgical planning system according to claim 1, wherein the segmentation takes soft tissues and/or vascular systems into consideration.

7. The surgical planning system according to claim 1, wherein a number of proposals are created for a segmentation using easily variable boundary conditions, and one, several, or all of the proposals are visualized for a selection.

8. The surgical planning system according to claim 1, wherein the processing circuitry provides for the simultaneous visualization of the 3D target data and the reconstruction of the segments.

9. The surgical planning system according to claim 1, wherein the 3D image data is data from computer tomography and/or MRT, MRT-angio and/or PET/CT, SPECT/CT, CT-angio, digital volume tomography, or 3D sonography.

10. The surgical planning system according to claim 1, wherein the 3D target data comprises copying and/or mirroring and/or relative repositioning of corresponding missing or damaged bone parts of the same patient or is generated from an anthropometric geometry database.

11. The surgical planning system according to claim 1, wherein data is provided for a robot-assisted surgery and/or real-time navigated surgery.

12. The use of a system according to claim 1, wherein the missing or damaged bone parts are parts of either a mandibula, a maxilla, a zygoma, a cranium, a hand bone, a foot bone, a tibia, a humerus, a femur, a radius or an ulna.

13. The use of a system according to claim 1, wherein the at least one osseous donor area is an iliac crest and/or a scapula and/or a fibula and/or a radius and/or a femur and/or a rib and/or a cranium and/or a tabula externa.

14. The use of a system according to claim 1, wherein the missing or damaged bone parts are parts of either a mandibula, a maxilla, a zygoma, a cranium, a hand bone, a foot bone, a tibia, a humerus, a femur, a radius or an ulna, and wherein the at least one osseous donor area is an iliac crest and/or a scapula and/or a fibula and/or a radius and/or a femur and/or a rib and/or a cranium and/or a tabula externa.

15. A surgical planning system for the reconstruction of missing or damaged bone parts, comprising:

processing circuitry for:

receiving 3D image data regarding at least one osseous donor area;

processing the 3D image data into structured 3D image data where osseous portions are distinguished from soft tissues and/or vascular systems;

reading in of 3D target data regarding a missing or damaged bone part;

obtaining one or more 3D target curves in relation to the 3D target data and the 3D image data of the at least one osseous donor area;

segmenting the structured 3D image data with the osseous portions of the at least one osseous donor area into segments, wherein the segments within the structured 3D image data are determined based on the 3D target data and an adaptation of sections of the one or more 3D target curves;

merging the segments into a reconstruction, wherein the segmentation adapts the one or more 3D target curves to 3D surfaces of the 3D target data;

creating structural data for a surgical template for use in a subsequent surgery; and causing simultaneous visualization of the 3D target data and the reconstruction of the segments, wherein the segmentation comprises adjusting minimum sizes for the segments, wherein the segmentation comprises adjusting maximum sizes for the segments, wherein the structural data for the surgical template is structural data for a 3D printer, wherein the segmentation takes soft tissues and/or vascular systems into consideration, wherein a number of proposals are created for a segmentation using easily variable boundary conditions, and one, several, or all of the proposals are visualized for a selection, wherein the 3D image data is data from computer tomography and/or MRT, MRT-angio and/or PET/CT, SPECT/CT, CT-angio, digital volume tomography, and 3D sonography, wherein the 3D target data comprises copying and/or mirroring and/or relative repositioning of corresponding missing or damaged bone parts of the same patient or is generated from an anthropometric geometry database, wherein data is provided for a robot-assisted surgery and/or real-time navigated surgery, wherein the missing or damaged bone parts are parts of either a mandibula, a maxilla, a zygoma, a cranium, a hand bone, a foot bone, a tibia, a humerus, a femur, a radius or an ulna, and wherein the at least one osseous donor area is an iliac crest and/or a scapula and/or a fibula and/or a radius and/or a femur and/or a rib and/or a cranium and/or a tabula externa.

* * * * *